United States Patent [19]
Vinot et al.

[11] Patent Number: 5,471,879
[45] Date of Patent: Dec. 5, 1995

[54] ULTRASONIC PROCESS FOR TESTING, BY IMMERSION, A METAL PIECE AND USE THEREOF

[75] Inventors: Jacques Vinot, Gilly/Isere; Christian Moisson, Cesarches; Christian Eymond, Albertville, all of France

[73] Assignees: Compagnie Europeene du Zirconium Cezus; Framatome, both of France

[21] Appl. No.: 120,083

[22] Filed: Sep. 13, 1993

[30] Foreign Application Priority Data

Sep. 14, 1992 [FR] France ................... 92 11117

[51] Int. Cl.⁶ ........................................... G01N 29/20
[52] U.S. Cl. ............... 73/622; 73/625; 73/628; 73/641; 73/642
[58] Field of Search ............... 73/622, 642, 625, 73/628, 641

[56] References Cited

U.S. PATENT DOCUMENTS

| | | | |
|---|---|---|---|
| 4,289,033 | 9/1981 | Prause et al. | 73/622 |
| 4,596,953 | 6/1986 | Nagasaka et al. | 73/622 |
| 4,665,734 | 5/1987 | Joet | 73/622 |
| 4,699,007 | 10/1987 | Kawashima et al. | 73/622 |
| 4,843,884 | 7/1989 | House et al. | 73/622 |
| 5,001,674 | 3/1991 | Kawasaki | 73/642 |
| 5,165,280 | 11/1992 | Sternberg et al. | 73/625 |

Primary Examiner—Richard Chilcot
Assistant Examiner—Eric S. McCall
Attorney, Agent, or Firm—Dennison, Meserole, Pollack & Scheiner

[57] ABSTRACT

The invention relates to an ultrasonic process for testing, by immersion, the soundness of a metal piece (26) using at least one transducer (21) emitting ultrasonic waves focused in the piece (26). There are a plurality of transducers (21) used. Each of the transducers having in the tested piece (26) a focal spot at −6 dB, the section of which, perpendicular to the axis of propagation of the waves is less than 40 mm2. The focal spots of the transducers (21) being distributed depending on the depth to be tested of the piece (26). Additionally, the invention describes a process to guarantee the soundness of the interior of a piece (26), in particular a bar made of a titanium alloy (26) of a diameter of between about 50 and 400 mm for use in aeronautics.

16 Claims, 1 Drawing Sheet

ULTRASONIC PROCESS FOR TESTING, BY IMMERSION, A METAL PIECE AND USE THEREOF

BACKGROUND OF THE INVENTION

1. Field of the Invention

The invention is applicable to the non-destructive testing of metal pieces, and more particularly to the ultrasonic checking thereof by immersion in a coupling liquid such as water.

The document FR-A-2650144 discloses an ultrasonic method for testing, by immersion, a metal piece using at least one transducer which emits ultrasonic waves into the piece. That document discloses the use of a transducer which focuses at a point inside the piece, the points of the emitting surface of that transducer being equidistant acoustically from the internal point.

Usually, the "focusing point" or focus of a transducer of this kind is surrounded by an acoustic volume comprising a focal spot which extends along the axis of propagation of the ultra-sound, and the geometry and acoustic structure of the focal spot make difficult and uncertain the ultrasonic testing of pieces such as thick bars made of titanium alloys intended for the manufacture of finished pieces or elements for use in aeronautics, the testing having to satisfy high quality requirements.

The inventor has sought ways of solving the corresponding problems, and of improving the reproducibility and accuracy of such ultrasonic testing by immersion.

SUMMARY OF THE INVENTION

The invention which solves the problem resides in an ultrasonic process for testing, by immersion, the condition, or soundness, of a metal piece using at least one transducer emitting ultrasonic waves which are focused in the piece, characterised in that a plurality of transducers is used, each having in the tested piece a focal spot at −6 dB, of which the section perpendicular to the axis of propagation of the waves is less than 40 mm2, the focal spots of said transducers being distributed in accordance with the depth which is to be tested of said piece.

Each transducer which focuses in the metal piece being tested, or in a control piece or sample piece of the same type and geometry for the testing operation which has a reference imperfection, has a focal spot around its point focus or focus of small volume, in which focal spot the amplitude of ultrasonic vibrations decreases as the distance from said focus increases. The focal spot is thus defined in dependency on the maximum decrease of said amplitude in relation to the amplitude in the focus, this decrease qualifying the state of vibrations of its surface. The level "−6 dB" thus corresponds to 50% relative amplitude. To accurately test the internal volume of the piece, it is necessary to have focal spots at −6 dB consisting firstly in volumes of vibration which are sufficiently concentrated transversely with vibration, that is to say with a section perpendicular to the axis of propagation of the ultra-sound of less than 40 mm2. At the same time, these focal spots which extend along the axis of propagation and which are typically bulbous or cylindrical in shape in their central region and tapering like a rugby ball on either side of that central region, are distributed in accordance with the depth to be tested in the piece.

The concentration of the focusing in the piece is preferably selected by limiting the section of the focal spot to less than 25 times the reflecting surface of a reference imperfection to be detected, less than 28.2 mm2, 19.6 mm2 or 12.5 mm, for example, depending on whether the imperfection is a flat-bottom hole of 1.2 mm, 1 mm or 0.8 mm in diameter respectively, or by limiting the section to less than 25 mm2 which permits an improvement in concentration suited to most ultrasonic tests on the soundness of metal pieces.

A thorough testing of the soundness of the interior of a piece, with the exception of a superficial zone of selected depth, means that the transducers used have focal spots, described hereinabove, whose extents become covered in accordance with their depths, that is to say their depth intervals in the piece. Hereinbelow, it will be seen that in the case of titanium alloys with high characteristics, the sum of the alloy elements of which titanium alloys usually exceeds 9% by mass, the problem of noise or grass which corresponds to successive reflections on the faces of crystals, and, it would seem, also to ultrasonic emissions at the tapering points or at the point of certain crystals entrained by vibration, is of very great significance, and results in more restrictive rules in instances where the testing has to be very accurate.

Generally speaking, focusing transducers comprise a piezoelectric crystal of a frequency suitable for ultrasonic resonance or vibration, typically between 2 and 20 MHz. According to a customary practice, a shock-absorber is provided behind the crystal and a focusing lens is provided in front of the crystal in a transducer, the assembly in the transducer casing thus comprising two interfaces for the crystal. The transducer has a central emission frequency and reflection frequency in the piece to be tested, that is to say the "frequency of the transducer" which differs from that of its vibrating crystal and is thus between 2 and 15 MHz.

The emitting surface of each focusing transducer, that is to say the emitting surface of its focusing lens according to the conventional practice, is preferably defined and obtained as a function of the geometry of the piece to be tested and on the depth to be tested or the depth of the focal spot in that piece. By knowing the position of the transducer in relation to the piece in the testing operation by immersion and the position of its focus in the piece, the other points on the emitting surface of the transducer ape necessarily in equiphasal positions on the path, or trajectory, of the focal spot.

In accordance with one particularly advantageous feature, the piezoelectric crystal itself comprises an emitting surface which focuses at equiphasal acoustic distances from the focus in the piece being tested, this crystal having intersecting grooves which form a grid and are filled with plastics material and open onto the emitting surface. The grooves of the piezoelectric material cause the plastics material to vibrate which couples well with water and damping is improved. With a comparable excitation, an energy beam is obtained which is typically 8 to 12 times greater than in accordance with conventional practice.

With respect to the requirements encountered within the ultrasonic testing on the soundness of pieces by immersion it is preferable to use longitudinal waves, each transducer emitting waves which are propagated in a direction close to a perpendicular to the surface of the piece and detecting the waves reflected in the piece.

A test is therefore carried out on bars made of a titanium alloy of a diameter of between 50 and 400 mm.

In the general case of transducers which focus at constant acoustic distances from the focus in the piece being tested, each transducer has a frequency which is preferably between 2 and 15 MHz.

In the case of the afore-mentioned titanium alloy bars, it has been found that it is more advantageous to use transducers with a frequency of between 3 and 8 MHz, their focal spots at −6 dB having a section perpendicular to the axis of propagation of the ultrasound which is less than or equal to 25 mm2. When the purpose is to improve the signal/noise ratio and thus improve the sensitivity with which imperfections reflecting the ultrasound are detected, it has been seen that in the case of titanium alloy bars the reduction of the observation depth interval of each transducer to a fraction of its focusing depth at −6 dB was of very great significance. Thus, for titanium alloy bars with a diameter of between 250 and 400 mm, the observation depth interval or "testing window" of each transducer is preferably controlled to a value between 1/15 and 1/2 and preferably between 1/15 and 1/8 of its focusing depth at −6 dB in the metal.

To carry out the testing operation, by immersion, of a titanium alloy bar, the soundness of the entire lower volume of the bar is effectively tested, with the exception of a superficial zone of internal depth 10 mm by displacing the set of transducers in relation to the piece in such a way as to obtain a testing pitch which in length is less than or equal to 0.7 times the square root of the section which is perpendicular to the axis of propagation of the focal spot at −6 dB of each transducer, that condition thus applying to the weakest section. The transducers which are equidistant acoustically have focal spots which are slightly oval, and in width/length are typically greater than 0.6, which allows a practical rule to be adopted for the transverse covering over of testing trajectories.

In the case of titanium alloy bars of a diameter of between 250 and 400 mm, with a relatively weak surface of curvature, the superficial zone which is not tested is of a depth which is selected between 1.5 and 10 mm, preferably using a transducer with an emitting surface associated with a piezoelectric crystal with level grooves filled with plastics material, if the depth is less than 3 mm. The entire internal volume is then tested, with the exception of the aforementioned superficial zone, by moving the set of transducers in translatory fashion parallel to the longitudinal axis of the bar and by simultaneously rotating the bar on itself in such a way as to carry out the testing along helicoidal trajectories of the transducers in relation to the bar, these trajectories having the same length pitch which is less than or equal to 0.7 times the square root of said section of the focal spot at −6 dB of each of the transducers.

The invention also related to use of the above-mentioned process according to any one of these practices for guaranteeing the soundness of the whole of the inside of a piece which is solid or tubular, with the exception of a superficial zone of that piece which is less than 10 mm in depth, this method of testing being qualified or referenced for each transducer in relation to a hole with a flat reflecting bottom which is less than or equal to 1.2 mm in diameter. In particular, in the case of a titanium alloy bar which is between 50 and 400 mm in diameter, and preferably using the afore-described features for testing the bars, this method is qualified in relation to a hole with a flat bottom which is less than or equal to 1 mm in diameter, and preferably between 0.7 and 1 mm.

The main advantage of the invention is that it provides an ultrasonic process for testing the soundness of the entire useful volume of a piece in relation to a reference imperfection of very small surface area, even in instances where the type and structure of the metal piece are unfavourable (pieces, and, in particular, bars of titanium alloy of high mechanical resistance) and in instances where, at the same time, a significant depth is to be tested (diameters 250 to 400 mm).

BRIEF DESCRIPTION OF THE DRAWINGS

FIG. 3 shows a transducer which focuses having an emitting crystal with intersecting grooves filled with plastics material, in axial section.

Figure 1:
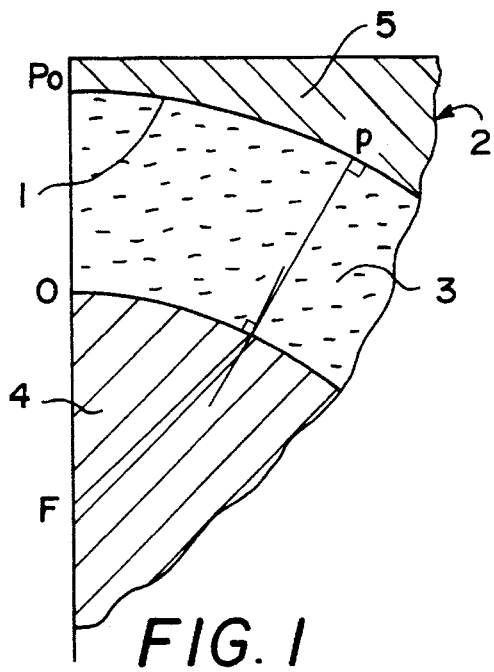
FIG. 1 shows a focusing transducer in a piece with constant acoustic distances, in axial semi-section.

1) In FIG. 1 it is possible to see the emitting surface 1 of the focusing transducer 2 which is immersed in water 3 above a bar 4 to be tested by ultra-sound. The wave emitted by the centre Po of the emitting surface 1 of the focusing lens 5 focuses in the piece at a same point F as the waves emitted by the other points such as P of the emitting surface 1, the requirement for a constant spacing between any P and F being satisfied.

Figure 2:
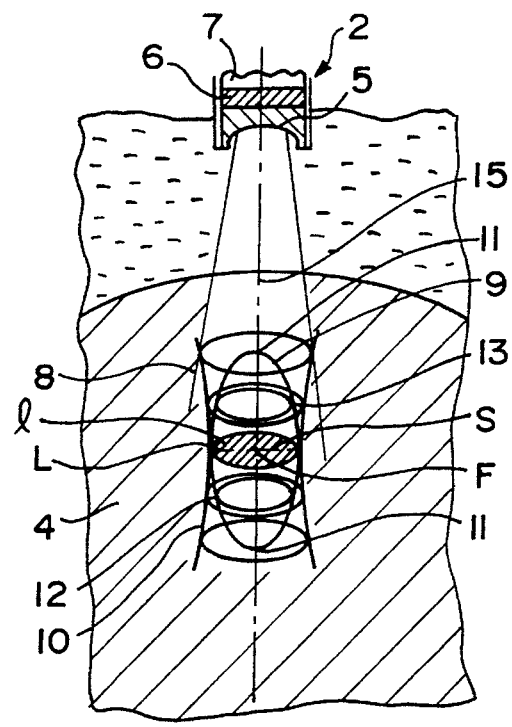
FIG. 2 shows the focal spot of a transducer such as this focusing inside a piece, with the transducer shown in axial section and the piece shown in transverse section, the focal spot being shown in isometric projection.

2) FIG. 2 is an illustration of the acoustic field obtained in the bar 4. The focusing transducer 2 comprises to the rear of its focusing lens 5 a piezoelectric resonant crystal 6 and a shock-absorber 7. The acoustic field 8 comprises a contour 9 which encloses the focus F, illustrated by way of its casing at −6 dB in relation to the focus F. This focal spot at −6 dB is shown as being that which is obtained, with the contour 10, with increase controlled as a function of depth, the focal spot 10 being quasi-cylindrical over a large part of its height, and here being slightly widened at the level of the tapered ends 11 of the spot 9 prior to correction. Moreover, the drawing shows the effect of controlling the observation depth interval of the transducer to a fraction of the focusing depth, that is to say the depth of the focal spot 9: when this interval is limited by the depth levels 12 and 13, before or after correction, the variations in width of the focal spot 9 or 10 are reduced within that range in correlation with the increase in the gain on either side of the focus F, the modification permitting an increase in the signal/noise ratio and thus an improvement in the sensitivity of the detection.

Figure 4:
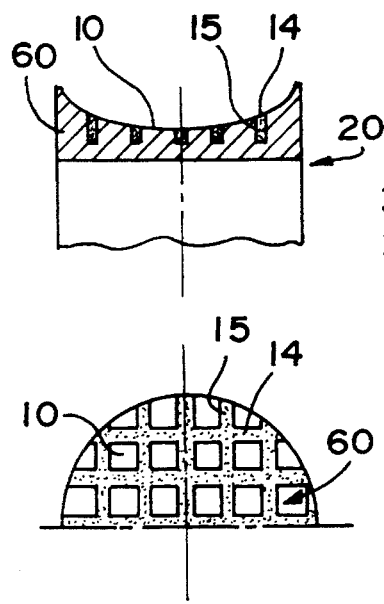
FIG. 4 shows a semi-view in plan of the emitting face of the crystal.

3) In FIGS. 3 and 4, it is possible to see a piezoelectric crystal 60 which is used as a focusing lens of the transducer 20, this transducer 20 comprising intersecting grooves 14 filled with plastics material 15, the grooves 14 passing over the emitting surface 10 which is at a constant acoustic distance away from an internal point in the piece to be tested by ultrasound by immersion. Performances with ultra-sound energy and shock-absorbing energy have been given hereinabove for such a crystal 60 and for such a transducer 20.

Figure 5:
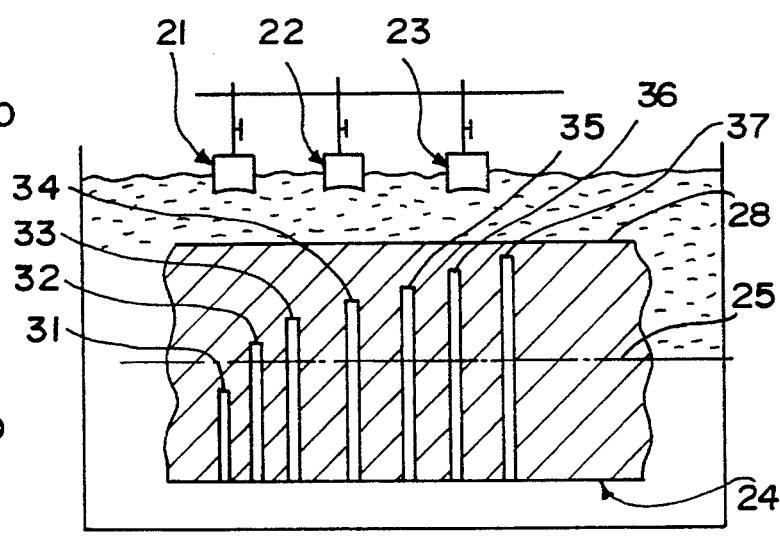
FIG. 5 shows an axial section of the reference bar, with a control testing device with 3 focusing transducers for a titanium alloy bar, the control operation being carried out on a control bar through which holes pass which have a flat reference bottom.
Figure 6:
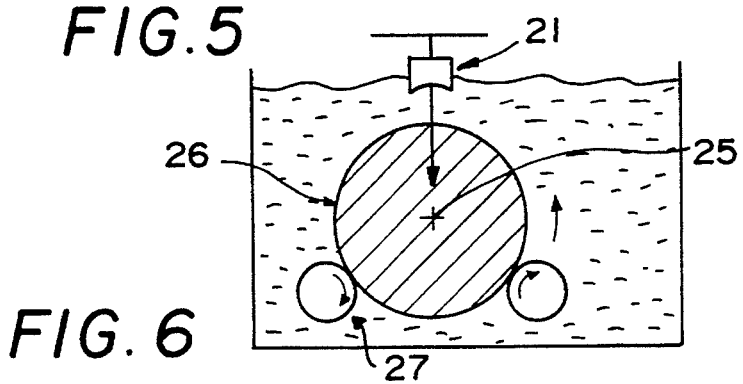
FIG. 6 shows an ultrasonic continuous testing device for a bar, in section perpendicular to the axis of the bar.

4) Ultrasonic testing for the soundness of titanium alloy bars of 330 mm in diameter (FIGS. 5 and 6)

The alloy is Ti with mean contents by mass of 6% Al and 4% V. The bars are intended for the manufacture of components for use in aeronautics. They have been worked in such a way that the imperfections which may be present in them and which are to be detected are cracks or inclusions which are usually elongate or oriented in the axial extent of the bars, the testing by way of radial ultrasonic waves thus being capable of detecting their axial reflecting surfaces.

For this test, three focusing transducers 21, 22, 23 are used which have emitting surfaces at a constant acoustic distance away from the focuses of staggered depth in the piece being tested, the transducers 21, 22, 23 of 5 MHz each having been prepared specially by a manufacturer and supplied with information relating to their focusing, and, in particular, to their focal spots at −6 dB.

For controlling the observation depth interval of each transducer and for controlling the increase as a function of the depth, a portion of bar 24 taken as a sample was used comprising seven radial flat bottom holes of staggered depth, the flat bottoms 31 to 37 of these holes of diameter 1.2 mm being of the following depths in relation to the probe generatrix 28 contained in their axial plan:

"31": 177 mm;
"32": 131 mm;
"33": 86 mm;
"34": 64 mm;
"35": 43 mm;
"36": 26 mm;
"37": 8 mm;

Coverings over in depth were provided between the observation intervals or "control windows", since each of the flat bottoms 33 and 35 is observed by two transducers, 21 and 22 and 22 and 23 respectively. The observations made using these flat bottom holes made it possible for the positions in depth of the focal spots of the three transducers 21, 22, 23 to be specified, the manufacturer's indications of depth being approximate due to the way in which they are analysed by detecting in the water waves transmitted through a portion of the bar limited by a flat lower face.

Table 1 groups the depth intervals of focal spots at −6 dB for three transducers, the observation intervals or "control windows" selected, and the main sizes of section S of the focal spots at 6-dB perpendicular to the axis of propagation (15) of the ultrasonic waves, these sections S being slightly oval and their length L and width 1 (FIG. 2) relating respectively to their perpendicular extent to the longitudinal axis 25 of the sample bar 24 or of the bar being tested 26 and the extent of that axis 25.

The ultrasonic testing operation of bars 26 (FIG. 6) is carried out by rotating each bar 26 on itself using rollers 27 at a peripheral speed of 1 m/s, the set of transducers 21 to 23 moving with translatory movement parallel to the axis 25, thereby providing a helicoidal exploration of pitch 2.27 mm, less than 0.7 times the square root of the section S of the focal spot of the transducer which tests the central region of the bar.

Testing 100% of the volume of the bars, with the exception of the surface layer of depth less than or equal to 6 mm, is thus done with good coverings by depth and in an axial direction. The ratio of the signal of the flat bottom hole of diameter 1.2 mm to the noise is 4 dB, or the noise itself is at the same level as the echo of a flat bottom hole of diameter 0.95 mm, ensuring the level of testing desired.

5) Complementary Control Test, relating to the same bars of diameter 330 mm

A fourth transducer of the same type as the transducers 21 to 23 and also 5 MHz, with a Focusing depth interval at −6 dB of 130 mm surrounding the axis 25 of the bar and a section of oval Focal spot of 7.6 mm×4.4 mm, a flat bottom hole of diameter 0.8 mm was taken as a control, this flat bottom being disposed at a depth of 151 mm. The observation depth interval was restricted to 146 to 156 mm in depth, that is to say to 1/13 of the depth interval at −6 dB of the transducer. A surprising improvement was then noted in the sensitivity of detection, the signal to noise ratio in relation to the flat bottom hole of diameter 0.8 mm being very good with a noise of the same level as with a flat bottom hole of diameter 0.5 mm. The supposed effect of this type of reduction to the observation interval was mentioned in relation to FIG. 2, the practical result is unexpected and enables the conclusion to be made that, even with smaller reductions to the observation interval, at the expense of increasing the number of transducers with staggered observation depth intervals, it is possible to observe improvements in the sensitivity of the ultrasonic testing and the guarantee of soundness in connection with this test.

TABLE I

| Ref. of trans-ducer | Depth Interval at −6 dB of focal spot | Obser-vation Depth Interval (mm) | Position in depth of focus (mm) | Section at −6 dB of focal spot | | |
|---|---|---|---|---|---|---|
| | | | | L (mm) | 1 (mm) | S (mm2) |
| 21 | 75–185 | 81–177 | 139 | 6 | 4 | 19.5 |
| 22 | 35– | 38– | 81 | 5 | 3.2 | 13 |
| 23 | 0–70 | 6–48 | 37 | 4.2 | 3.8 | 12.6 |

We claim:

1. An ultrasonic process for testing, by immersion, a condition of a metal piece, comprising the steps of:

providing a plurality of transducers;

activating the plurality of transducers to emit ultrasonic waves along respective axes of propagation; and focusing the ultrasonic waves on the metal piece;

wherein each of said plurality of transducers has a focal spot at −6 dB, each said focal spot having a section, perpendicular to its respective axis of propagation, which is no greater than 25 mm$^2$, said focal spots of said plurality of transducers being distributed in accordance with a depth of said metal piece to be tested;

wherein said focal spots of said transducers at −6 dB become covered in accordance with respective depths of said focal spots in said metal piece;

wherein each of said plurality of transducers has an emitting surface, each said emitting surface having a point distanced acoustically such that, as measured in water and in said metal piece, distances from centers of said focal spots are identical;

wherein said ultrasonic waves comprise longitudinal ultrasonic waves, each of said plurality of transducers emitting ultrasonic waves which are propagated in a direction adjacent to a line perpendicular to a surface of the metal piece, each of said plurality of transducers detecting waves reflected by said metal piece;

wherein said metal piece comprises a titanium alloy bar having a diameter of 50 mm. to 400 mm.;

wherein each of said plurality of transducers has a frequency of 3 MHz to 8 MHz;

said method comprising the further step of controlling an observation depth interval of each of said plurality of transducers to a fraction of a focusing depth at −6 dB of each of said plurality of transducers, thereby improving the accuracy of the testing operation;

wherein said metal piece comprises a bar having a diameter of 250 mm. to 400 mm., said observation depth interval being controlled to 1/15 to 1/2 of the focusing depth at −6 dB; and wherein an entire internal volume of said bar is tested, except for a superficial zone having a depth of 1.5 mm. to 10 mm., by displacing each of said plurality of transducers in translatory movement parallel to a longitudinal axis of said bar, and simultaneously rotating said bar with respect to itself in such a way as to carry out a check along helicoidal trajectories of said plurality of transducers relative to said bar, said helicoidal trajectories having identical pitches which, in length, are no greater than 0.7 times a square root of the section of the focal spot −6 dB of each of plurality of said transducers.

2. An ultrasonic process for testing, by immersion, a condition of a metal piece, comprising the steps of:

providing a plurality of transducers;

activating the plurality of transducers to emit ultrasonic waves along respective axes of propagation; and focusing the ultrasonic waves on the metal piece;

wherein each of said plurality of transducers has a frequency of 3 to 8 MHz, and a focal spot at −6 dB, each said focal spot having a section, perpendicular to its axis of propagation, of less than 25 mm$^2$, said focal spots of said transducers being distributed in accordance with a depth of said metal piece which is to be tested, said focal spots of said transducers becoming covered after an observation depth interval of each of said transducers is controlled to a fraction of a focusing depth at −6 dB.

3. The process of claim 2, wherein said section of each said focal spot is less than 25 times a reflecting surface of a reference imperfection to be detected.

4. The process of claim 3, wherein each of said plurality of transducers has an emitting surface, each said emitting surface having a point which is distanced acoustically such that, as measured in water and in the metal piece, distances from centers of said focal spots are identical.

5. The process of claim 4, wherein each said emitting surface is associated with a piezoelectric crystal having intersecting grooves filled with plastic material and opening onto said emitting surface.

6. The process of claim 4, wherein said ultrasonic waves comprise longitudinal ultrasonic waves, each of said plurality of transducers emitting ultrasonic waves which are propagated in a direction adjacent to a line perpendicular to a surface of the metal piece, each of said plurality of transducers detecting waves reflected from said metal piece.

7. The process of claim 6, wherein said metal piece comprises a titanium alloy bar having a diameter of 50 to 400 mm.

8. The process of claim 7, wherein said metal piece comprises a bar having a diameter of 250 to 400 mm., and wherein an observation depth interval of each of said plurality of transducers is controlled to 1/15 to 1/2 of a focusing depth at −6 dB.

9. The process of claim 8, wherein an entire internal volume of the bar is tested, except for a superficial zone which is less than 10 mm. in depth, by displacing an assembly of said plurality of transducers relative to the metal piece in such a way as to obtain a testing pitch which has a length no greater than 0.7 times a square root of the section of the focal spot at −6 dB of each of said plurality of transducers.

10. The process of claim 9, comprising the further step of controlling the observation depth interval of each of said plurality of transducers by using a portion of the bar immersed, said portion of the bar immersed being discontinuous so as to form a plurality of radial holes, each of said plurality of radial holes having an axial reflecting bottom of a diameter no greater than 1.2 mm., said method comprising the further step of detecting at least one of said reflecting bottoms with at least one of said plurality of transducers.

11. The process of claim 10, wherein at least one of said plurality of radial holes has an axial reflecting bottom of a diameter between 0.7 mm. and 1 mm.

12. The process of claim 8, wherein an entire internal volume of the bar is tested, except for a superficial zone having a depth of between 1.5 mm. and 10 mm., by displacing each of said plurality of transducers in translatory movement parallel to a longitudinal axis of the bar, and simultaneously rotating the bar with respect to itself in such a way as to carry out a check along helicoidal trajectories of said plurality of transducers relative to said bar, said helicoidal trajectories having identical pitches which, in length, are no greater than 0.7 times a square root of said section of the focal spot at −6 dB of each of said plurality of transducers.

13. The process of claim 6, wherein each of said plurality of transducers has a frequency of 2 MHz. to 15 MHz.

14. An ultrasonic process for testing, by immersion, a condition of a metal piece, comprising the steps of:

providing a plurality of transducers;

activating the plurality of transducers to emit ultrasonic waves along respective axes of propagation; and focusing the ultrasonic waves on the metal piece;

wherein each of said plurality of transducers has a focal spot at −6 dB, each said focal spot having a section, perpendicular to its respective axis of propagation, which is no greater than 25 mm$^2$, said focal spots of said plurality of transducers being distributed in accordance with a depth of said metal piece to be tested;

wherein said focal spots of said transducers at −6 dB become covered in accordance with respective depths of said focal spots in said metal piece;

wherein each of said plurality of transducers has an emitting surface, each said emitting surface having a point distanced acoustically such that, as measured in water and in said metal piece, distances from centers of said focal spots are identical;

wherein said ultrasonic waves comprise longitudinal ultrasonic waves, each of said plurality of transducers emitting ultrasonic waves which are propagated in a direction adjacent to a line perpendicular to a surface of the metal piece, each of said plurality of transducers detecting waves reflected by said metal piece;

wherein said metal piece comprises a titanium alloy bar having a diameter of 50 mm. to 400 mm.;

wherein each of said plurality of transducers has a frequency of 3 MHz to 8 MHz;

said method comprising the further step of controlling an observation depth interval of each of said plurality of transducers to a fraction of a focusing depth at −6 dB of each of said plurality of transducers, thereby improving the accuracy of the testing operation;

wherein said metal piece comprises a bar having a diameter of 250 mm. to 400 mm., said observation depth interval being controlled to $\frac{1}{15}$ to $\frac{1}{2}$ of the focusing depth at −6 dB; and wherein an entire internal volume of said bar is tested, except for a superficial zone having a depth of less than 10 mm., by displacing an assembly of said plurality of transducers relative to said metal piece in such a way as to obtain a testing pitch which has a length no greater than 0.7 times a square root of the section of the focal spot at −6 dB of each of said plurality of transducers.

15. The method claim 14, comprising the further step of controlling the observation depth interval of each of said plurality of transducers by using a portion of the bar immersed, said portion of the bar immersed being discontinuous so as to form a plurality of radial holes, each of said plurality of radial holes having an axial reflecting bottom of a diameter no greater than 1.2 mm., said method comprising the further step of detecting at least one of said reflecting bottoms with at least one of said plurality of transducers.

16. The method of claim 15, wherein at least one of said plurality of radial holes has an axial reflecting bottom of a diameter between 0.7 mm. and 1 mm.

* * * * *